(12) United States Patent
Safo et al.

(10) Patent No.: US 10,858,331 B1
(45) Date of Patent: Dec. 8, 2020

(54) ESTER NITRATES DERIVATIVES OF AROMATIC ALDEHYDES WITH MULTIPLE PHARMALOGIC PROPERTIES TO TREAT SICKLE CELL DISEASE

(71) Applicant: VIRGINIA COMMONWEALTH UNIVERSITY, Richmond, VA (US)

(72) Inventors: Martin Safo, Richmond, VA (US); Yan Zhang, Glen Allen, VA (US); Jurgen Venitz, Richmond, VA (US); Richmond Danso-Danqua, Henrico, VA (US); Tanvi Deshpande, Somerville, MA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/987,609

(22) Filed: Aug. 7, 2020

Related U.S. Application Data

(63) Continuation of application No. 14/913,180, filed as application No. PCT/US2014/052099 on Aug. 21, 2014, now Pat. No. 10,800,751.

(60) Provisional application No. 61/869,162, filed on Aug. 23, 2013.

(51) Int. Cl.
*C07D 307/58* (2006.01)
*C07D 213/30* (2006.01)

(52) U.S. Cl.
CPC ......... *C07D 307/58* (2013.01); *C07D 213/30* (2013.01)

(58) Field of Classification Search
CPC .......................... C07D 307/58; C07D 213/30
See application file for complete search history.

(56) References Cited

FOREIGN PATENT DOCUMENTS

GB      1539733 A      1/1979

OTHER PUBLICATIONS

Nnamani et al: "Pyridyl Derivatives of Benzaldehyde as Potential Antisickling Agents", Chemistry & Biodiversity 2008, vol. 5, No. 9, pp. 1762-1768.
Modak et al: "An efficient dehydroxymethylation reaction by a palladium catalyst," Chem. Comm. 2013, vol. 29, pp. 252-254.

*Primary Examiner* — Yong S. Chong
(74) *Attorney, Agent, or Firm* — W&C IP

(57) ABSTRACT

The invention provides new aromatic aldehyde compounds that have greater potency in increasing the affinity of Hb for oxygen, greater potency for preventing sickling, and additional pharmacologic properties that ameliorate other symptoms of SCD. The invention further provides methods for treating SCD by providing a subject having SCD with a compound according to the invention.

2 Claims, 5 Drawing Sheets

ESTER NITRATES DERIVATIVES OF AROMATIC ALDEHYDES WITH MULTIPLE PHARMALOGIC PROPERTIES TO TREAT SICKLE CELL DISEASE

BACKGROUND OF THE INVENTION

Field of the Invention

The invention relates to aromatic aldehydes and their use in the treatment of Sickle Cell Disease.

Summary of the Related Art

Sickle cell disease (SCD) is the consequence of substitution of Glu by Val in the $6^{th}$ position of the β-globin chain of hemoglobin (Hb) resulting in the formation of sickle Hb (HbS). Intracellular polymerization of deoxygenated sickle Hb into long, rigid and insoluble fibres causes the pathophysiology associated with SCD; facilitating a cascade of adverse events that include decreased nitric oxide (NO) bioavailability, endothelial cell activation, compensatory vasoconstriction, increase in neutrophil count, adhesion of red blood cells (RBCs) to tissue endothelium, vaso-occlusionand impaired microvascular blood flow. The clinical condition is characterized by chronic hemolytic anemia, frequent and severe painful crises, and multi-system pathology that impact nearly every organ.

Individuals with SCD have shown significant levels of pro-inflammatory cytokines, such as TNF-α which can trigger the painful vaso-occlusive crises and lead to the emergence of infectious and inflammatory episodes. TNF-α also stimulates production of free radicals and other inflammatory mediators, such as IL-1 and PGE2, and induce changes in coagulant and anticoagulant properties. Individuals with SCD have also shown decreased NO physiological levels in vascular endothelium that have also been linked to hemolysis, inflammation, vaso-occlusion and multiple organ stress. Produced naturally by the vascular endothelium, NO provides favorable microvasculature effects (i.e., dilation and increased blood flow), and also possesses anti-inflammatory properties.

Hydroxyurea (HU) is the only drug approved for treating SCD. When metabolized in vivo it releases NO which is responsible for inducing gamma globin expression and the formation of fetal Hb (HbF). Several NO-donor compounds, such as S-nitrosocysteine, detaNONOate and thalidomides have also been shown to increase gamma-globin expression. HbF is able to prevent RBC sickling by inhibiting HbS polymerization. The NO also has a direct positive vasodilation and anti-inflammation effects, as well as inhibition of platelet aggregation; reducing the severity and duration of vaso-occlusive crises. Nonetheless, it has been reported that HU treatment stimulates the production of pro-inflammatory cytokines, such as TNF-α, IL-1A, IL-1B, etc., counteracting the beneficial effects of the drug.

Delivery of oxygen to tissues is partly influenced by the affinity of Hb for oxygen. In normal circulation, oxygen is increasingly released in the following order—in larger vessels, at the arterioles, and at the capillaries. However, in patients with SCD, the existing compensatory low oxygen affinity ($P_{50}=32\pm2$ mm Hg; normal $P_{50}=26\pm2$ mm Hg), paradoxically causes more oxygen to be released at the arteries and arterioles. Vasoconstriction, which occurs at the arterioles to counteract this process, exacerbates the untoward cell sickling, vaso-occlusion, and inefficient tissue oxygenation at the capillaries. Several aromatic aldehydes, such as vitamin B6 (pyridoxal), vanillin, pyridyl derivatives of vanillin (INN compounds), 12C79 and 5-HMF have been studied that show promise in preventing tissue hypoxia by increasing the oxygen affinity of sickle Hb and ensuring availability of more oxygen at the capillaries. Some of these compounds also stercospecifically inhibit polymer formation. 5HMF, a non-toxic by-product of sugar metabolism is currently being studied by NIH/Baxter for treating SCD.

There is a need for new compounds that have greater potency in increasing the affinity of Hb for oxygen, greater potency for preventing sickling, and additional pharmacologic properties that ameliorate other symptoms of SCD.

BRIEF SUMMARY OF THE INVENTION

The invention relates to aromatic aldehydes and their use in the treatment of Sickle Cell Disease. The invention provides new compounds that have greater potency in increasing the affinity of Hb for oxygen, greater potency for preventing sickling, and additional pharmacologic properties that ameliorate other symptoms of SCD. The invention further provides methods for treating SCD by providing a subject having SCD with a compound according to the invention.

In a first aspect, the invention provides new anti-sickling aromatic aldehydes that have greater potency for increasing the affinity of hemoglobin (Hb), and especially sickle cell Hb (scHb) and/or reducing the ability of scHb to polymerize, thus reducing the sickling of sickle red blood cells.

Compounds according to the invention have the formula:

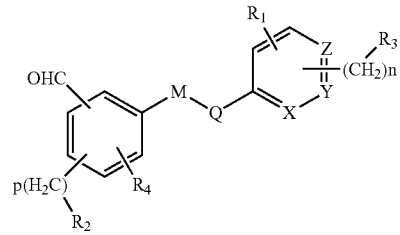

wherein R1 and R4 are the same or different and are H, OH, alkyl, alkoxy, halogen, aryl or O-aryl; and M and Q are different and are O or $(CH_2)q$; and R2 and R3 are the same or different and are H or OH; and X or Y or Z are the same or different and are C or N; and n is 0-5; and p is 0-5; and q is 0-5; with the proviso that when M is O, then either n is 1-5 or R1 is not H; and salts thereof.

Representative compounds selected from the group above include:

TD-7

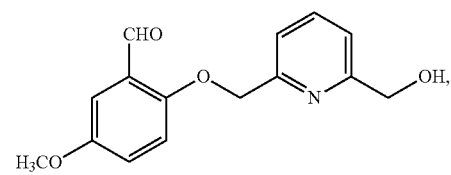

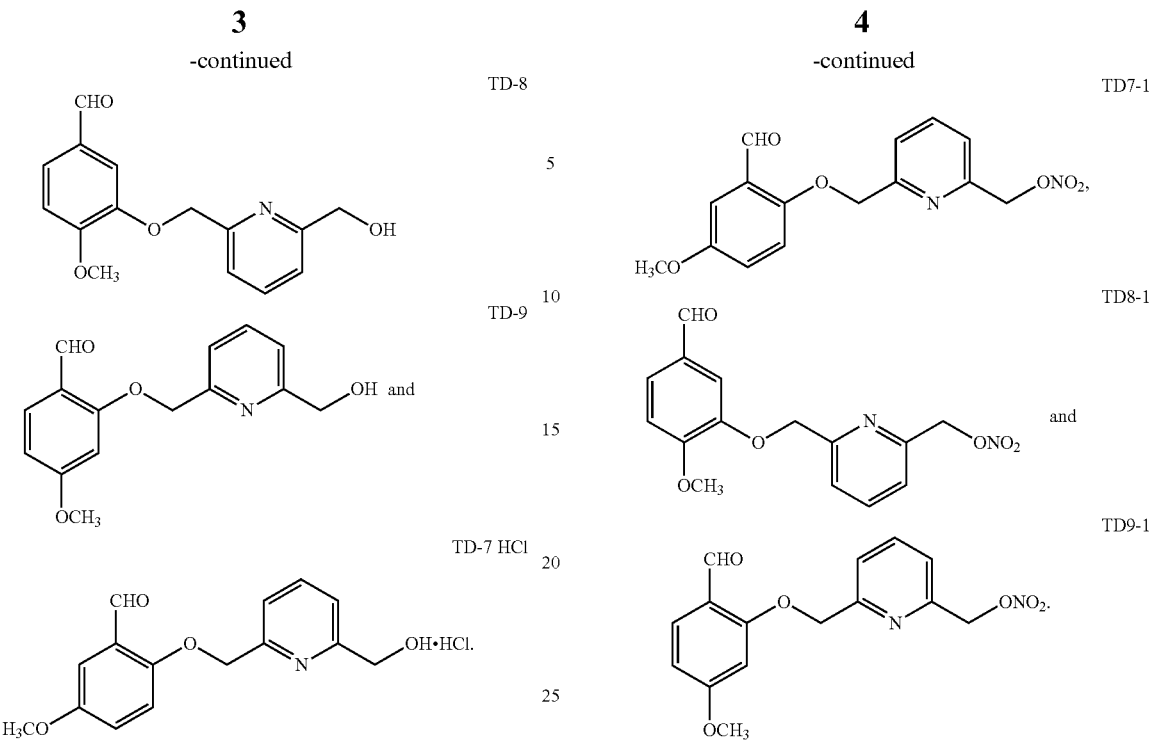

In a second aspect, the invention provides new aromatic aldehydes that are metabolized to produce NO$_2$ and anti-sickling aromatic aldehydes. Compounds according to this aspect have a structure selected from:

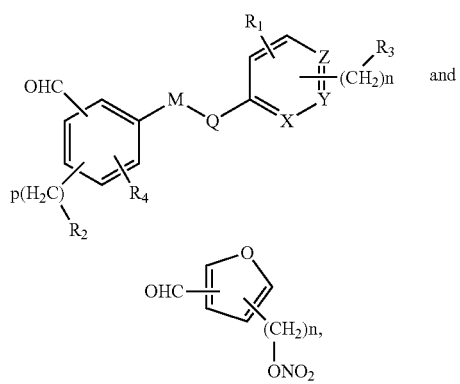

wherein R1 and R4 are the same or different and are H, OH, alkyl, alkoxy, halogen, aryl or O-aryl; and M and Q are different and are O or (CH$_2$)q; and R2 and R3 are the same and are ONO$_2$ or different with either as ONO$_2$ and the other as H or OH; and X or Y or Z are the same or different and are C or N; and n is 0-5; and p is 0-5; and q is 0-5; and salts thereof. In some embodiments, R1 is H; and M is 0; and R2 is H; and R3 is ONO$_2$; and p is 0.

Representative compounds selected from the group above include:

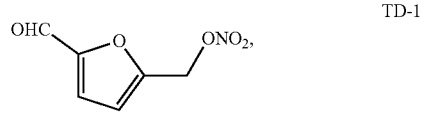

In a third aspect, the invention provides methods for treating a subject having sickle cell disease (SCD), comprising administering to the subject a therapeutically effective amount of one or more compound selected from the compounds according to the first or second aspect of the invention.

DETAILED DESCRIPTION OF THE PREFERRED EMBODIMENTS

Figure 1:
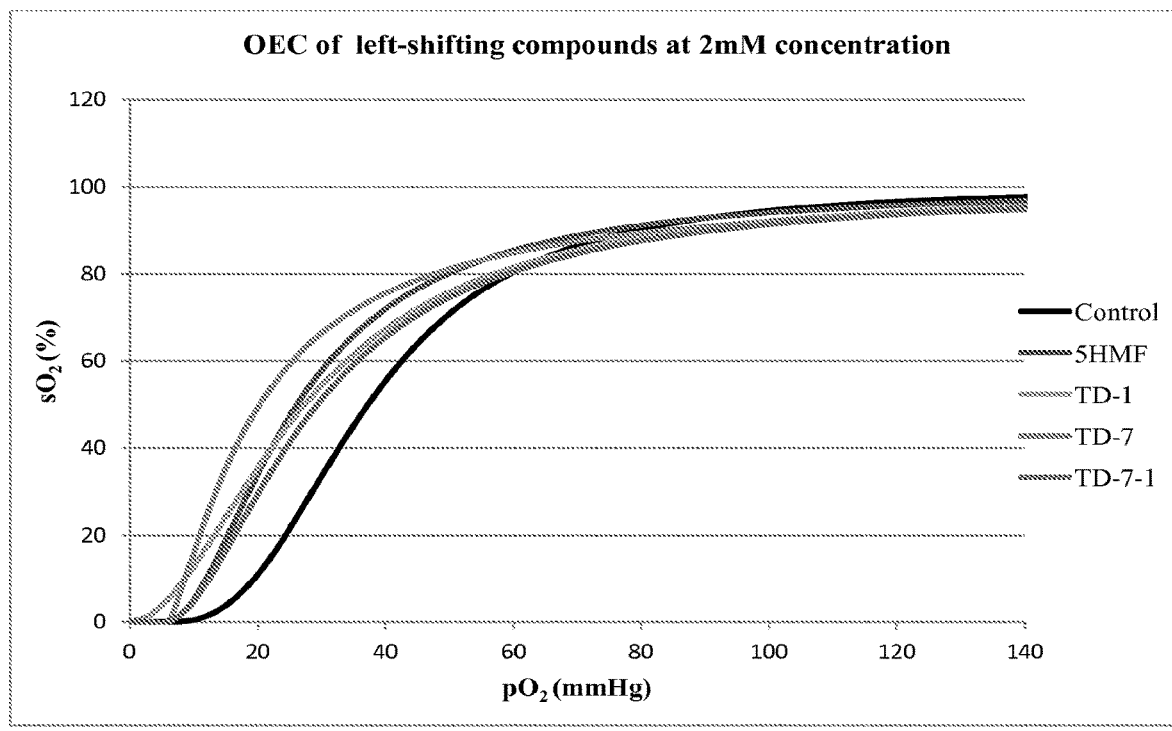
FIG. 1 shows results of oxygen equilibrium curve studies for 5-HMF and compounds TD-7, TD-7-1, TD-8, TD-8-1, TD-9 and TD-9-1.

The invention relates to aromatic aldehydes and their use in the treatment of Sickle Cell Disease. The invention provides new compounds that have greater potency in increasing the affinity of Hb for oxygen, greater potency for preventing sickling, and additional pharmacologic properties that ameliorate other symptoms of SCD. The invention further provides methods for treating SCD by providing a subject having SCD with a compound according to the invention.

In a first aspect, the invention provides new anti-sickling aromatic aldehydes that have greater potency for increasing the affinity of hemoglobin (Hb), and especially sickle cell Hb (scHb) and/or reducing the ability of scHb to polymerize, thus reducing the sickling of sickle cell red blood cells. Compounds according to the invention have the formula:

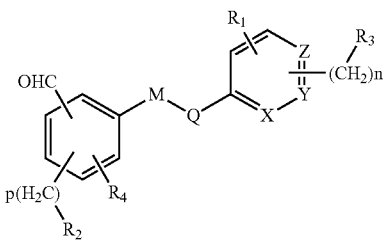

wherein R1 and R4 are the same or different and are H, OH, alkyl, alkoxy, halogen, aryl or O-aryl; and M and Q are different and are O or $(CH_2)q$; and R2 and R3 are the same or different and are H or OH; and X or Y or Z are the same or different and are C or N; and n is 0-5; and p is 0-5; and q is 0-5; with the proviso that when M is 0, then either n is 1-5 or R1 is not H; and salts thereof.

Representative compounds selected from the group above include:

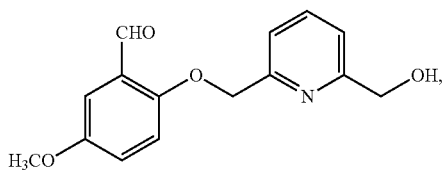

TD-7

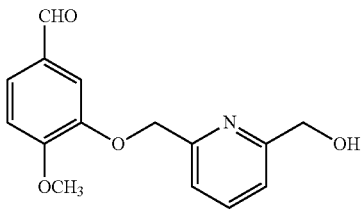

TD-8

TD-9

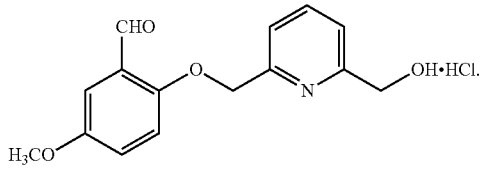

TD-7 HCl

In a second aspect, the invention provides new aromatic aldehydes that are metabolized to produce $NO_2$ and anti-sickling aromatic aldehydes. Compounds according to this aspect have a structure selected from:

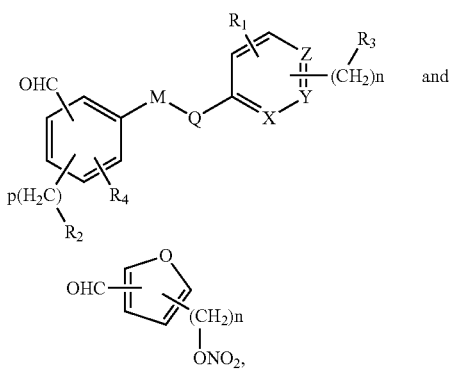

wherein R1 and R4 are the same or different and are H, OH, alkyl, alkoxy, halogen, aryl or O-aryl; and M and Q are different and are O or $(CH_2)q$; and R2 and R3 are the same and are $ONO_2$ or different with either as $ONO_2$ and the other as H or OH; and X or Y or Z are the same or different and are C or N; and n is 0-5; and p is 0-5; and q is 0-5; and salts thereof. In some embodiments, R1 is H; and M is 0; and R2 is H; and R3 is $ONO_2$; and p is 0; and salts thereof.

Representative compounds selected from the group above include:

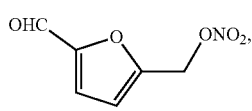

TD-1

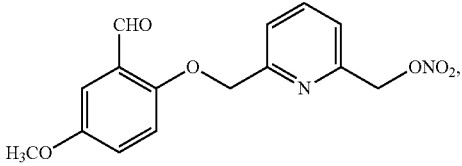

TD-7-1

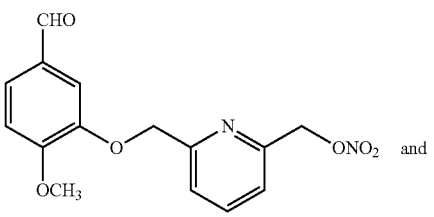

TD8-1

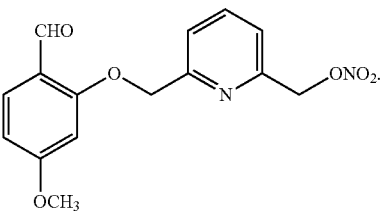

TD9-1

In a third aspect, the invention provides methods for treating a subject having sickle cell disease (SCD), comprising administering to the subject a therapeutically effective amount of one or more compound selected from the compounds according to the first or second aspect of the invention.

In some embodiments the subject is administered from about 20 mg to about 500 mg of the compound. In some embodiments the subject is administered from about 20 mg to about 300 mg of the compound. In some embodiments the subject is administered from about 20 mg to about 200 mg of the compound. In some embodiments the subject is administered from about 20 mg to about 100 mg of the compound. In some embodiments the subject is administered from about 20 mg to about 50 mg of the compound.

In some embodiments the subject is administered from about 100 mg to about 500 mg of the compound. In some embodiments the subject is administered from about 100 mg to about 300 mg of the compound. In some embodiments the subject is administered from about 100 mg to about 200 mg of the compound.

In some embodiments the subject is administered from about 200 mg to about 500 mg of the compound. In some embodiments the subject is administered from about 200 mg to about 300 mg of the compound.

In some embodiments the subject is administered from about 500 mg to about 10,000 mg of the compound. In some embodiments the subject is administered from about 1,000 mg to about 10,000 mg of the compound. In some embodiments the subject is administered from about 5,000 mg to about 10,000 mg of the compound.

Administration of the compounds can be by any suitable route, including, without limitation, parenteral, oral, sublingual, transdermal, topical, intranasal, inhalation, intratracheal, or intrarectal. In some preferred embodiments, administration is orally, by injection, or by inhalation.

The compounds used in the present invention may be present in any suitable diluent (including water), carrier or excipient.

The compounds used in the method of the present invention may form salts which are also within the scope of this invention. The term "salt(s)", as employed herein, denotes acidic and/or basic salts formed with inorganic and/or organic acids and bases. Pharmaceutically acceptable (i.e., non-toxic, exhibiting minimal or no undesired toxicological effects, physiologically acceptable) salts are preferred.

As used herein, the term "pharmaceutically acceptable salts" is intended to mean salts that retain the desired biological activity of the compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and dip henylacetate).

A "therapeutically effective amount" is an amount sufficient to alleviate or eliminate signs or symptoms of the disease.

Figure 5A:
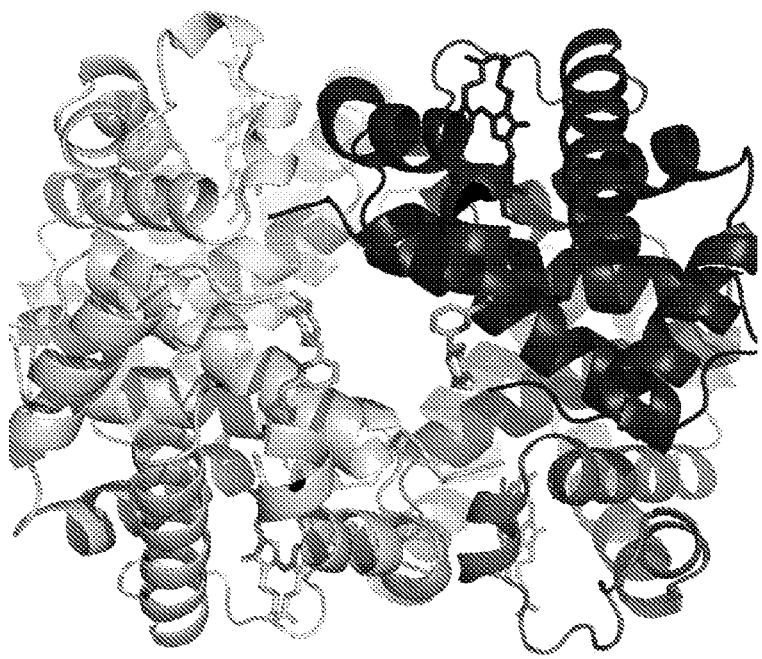
FIG. 5A shows binding of TD-7 (green) in deoxyHb.
Figure 5B:
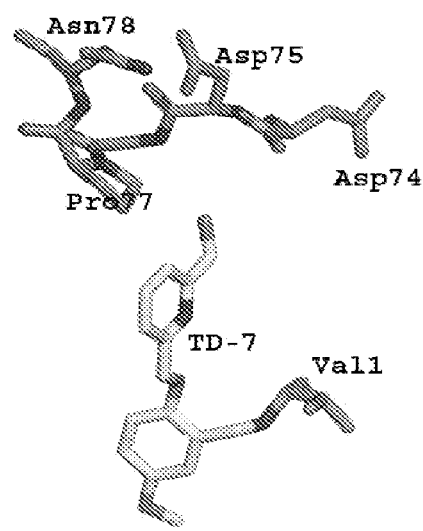
FIG. 5B shows a close view of TD-7 (yellow) interaction with the αF helix of the protein (green)

Without wishing to be bound by theory, we have determined the binding of TD-7 in deoxyHb to help elucidate its antisickling activity. Two molecules of TD-7 bind in a symmetry-related fashion at the α-cleft of the Hb, the aldehydes forming Schiff-base interaction with the two α-subunits N-terminal Vall nitrogens (FIG. 5A). Formation of the Schiff-base disposes the methoxy-pyridine-methoxyl substituent group toward the mouth of the central water cavity, where the hydroxyl of the methoxyl makes hydrogen-bond interactions with the amide nitrogen and oxygen atoms of aAsp75 and aAsp74, respectively (FIG. 5B); both residues located on the aF-helix. These interactions appear to perturb the aF-helix, as well as result in a significant conformational change in the side-chain of aAsn78. The aF-helix residue, Asn78 has been implicated in stabilizing the Hb S fiber, and the Hb variant, Stanclyville (aAsn78 aLsy78) is known to inhibit Hb S polymerization and RBS sickling.[20] Thus, not only does TD-7 increase the oxygen affinity of Hb by binding at the α-cleft and restraining the two α-subunits from transitioning from the oxyHb to the deoxy Hb conformation as previously described for 5HMF; based on the structure it seems that the improved potency of TD-7 is also in part due to increased perturbation of the aF-helix that leads to increased destabilization of the aF-helix mediated polymer contact.

The following examples are provided to further illustrate certain preferred embodiments of the invention and are not intended to be construed as limiting the scope of the invention.

Synthesis Example 1

5-Nitrooxymethyl furfural (TD-1)

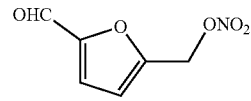

Compound TD-1 was prepared according to literature procedure for a similar compound. (Gavrila, A.; Andersen, L.; Skrydstrup, T., Tetrahedron Lett. 2005, 46, 6205-6207.)

Trifluoroacetic anhydride (5.5 mL, 2 mmol) was added to a suspension of lithium nitrate (2.7 g, 2 mmol) in anhydrous $CH_3CN$ (30 mL) at 20° C. The reaction mixture was stirred until clear (30 min) and cooled to 0° C. (ice-bath). Sodium carbonate (4.2 g, 2 mmol) and 5-(hydroxymethyl) furfural (2.5 g, 1 mmol) were added together and the reaction mixture was allowed to stir for 7 h at 0° C. (ice-bath). The reaction mixture was poured into an ice-cold solution of saturated $NaHCO_3$ and extracted with EtOAc (2×10 mL). The combined organic portion was washed with brine (10 mL), dried over $Na_2SO_4$ and evaporated under reduced pressure to yield a crude product. The crude residue was purified by column chromatography (petroleum ether/EtOAc; 2:1) to afford 2.9 g (85%) of TD-1 as a colorless viscous oil: IR (KBr, $cm^{-1}$): 1678 (C=O), 1631, 1276 ($NO_2$), 845 (ON); $^1$H-NMR ($CDCl_3$): δ 5.48 (s, 2H, $CH_2$), 6.73 (d, J=3.5 Hz, 1H, ArH), 7.25 (d, J=3.6, 1H, ArH), 9.68 (s, 1H, CHO); $^{13}$C-NMR ($CDCl_3$): δ 177.9, 153.4, 151.5, 120.9, 114.5, 65.4. Anal. Calcd for ($C_6H_5NO_5$) C, 42.12; H, 2.95; N, 8.19. Found: C, 42.02; H, 2.86; N, 8.26. The purity of the compound was checked by HPLC and was found to be 98.8% pure.

Synthesis Example 2

2-((6-(Hydroxymethyl)pyridin-2-yl)methoxy)-5-methoxybenzaldehyde (TD-7)

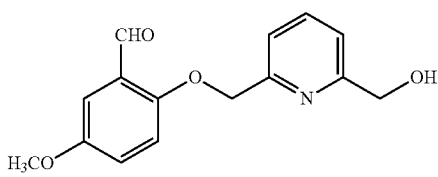 [SMILES: COc1ccc(OCc2cccc(CO)n2)c(C=O)c1]

Compound TD-7 was prepared according to literature procedure for a similar compound. (Nnamani, I. N.; Joshi, G. S.; Danso-Danquah, R.; Abdulmalik, O.; Asakura, T.; Abraham, D. J.; Safo, M. K., *Chem. Biodivers.* 2008, 5, 1762-1769.)

A mixture of 2-hydroxy-5-methoxybenzaldehyde (0.20 mL, 1.5 mmol), 6-(bromomethyl)-2-pyridinemethanol (0.30 g, 1.5 mmol), and $K_2CO_3$ (0.25 g, 1.8 mmol) in anhydrous DMF (20 mL) was allowed to stir at room temperature for 12 h. The reaction mixture was diluted with EtOAc (20 mL), washed with $H_2O$ (2×20 mL), brine (2×10 mL), dried over $Na_2SO_4$ and evaporated under reduced pressure to yield a crude product. The residue was purified by column chromatography (petroleum ether/EtOAc; 1:1) to yield 0.32 g (78%) of TD-7 as a yellow-colored solid: mp 84-85° C.; IR (KBr, cm$^{-1}$): 3396 (0-H), 1678 (C=O); $^1$H-NMR (CDCl$_3$): δ 3.51 (s, 1H, OH), 3.81 (s, 3H, OCH$_3$), 4.79 (s, 2H, CH$_2$), 5.29 (s, 2H, CH$_2$), 6.99 (d, J=9.0 Hz, 1H, ArH), 7.09-7.13 (dd, J=9.0, 3.2 Hz, 1H, ArH), 7.21 (d, J=7.7 Hz, 1H, ArH), 7.37 (d, J=3.2 Hz, 1H, ArH), 7.43 (d, J=7.6 Hz, 1H, ArH), 7.74 (t, 1H, ArH), 10.58 (s, 1H, CHO); $^{13}$C-NMR (CDCl$_3$): δ 189.24, 158.80, 155.61, 154.17, 154.17, 137.66, 125.56, 123.40, 119.84, 119.64, 114.92, 110.917, 71.65, 64.02, 55.86. MS (ESI) m/z found 274.15 (M+H)$^1$, 296.14 (M+Na)$^1$. The purity of the compound was checked by HPLC and was found to be 97.8% pure.

Synthesis Example 3

2-((6-(Hydroxymethyl)pyridin-2-yl)methoxy)-4-methoxybenzaldehyde (TD-9)

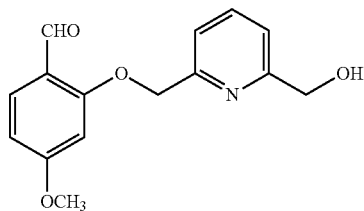 [SMILES: COc1ccc(C=O)c(OCc2cccc(CO)n2)c1]

Compound TD-9 was prepared according to literature procedure for a similar compound. (Nnamani, I. N.; Joshi, G. S.; Danso-Danquah, R.; Abdulmalik, O.; Asakura, T.; Abraham, D. J.; Safo, M. K., *Chem. Biodivers.* 2008, 5, 1762-1769.)

A mixture of 2-hydroxy-4-methoxybenzaldehyde (113 mg, 0.74 mmol), 6-(bromomethyl)-2-pyridinemethanol (150 mg, 0.74 mmol), and $K_2CO_3$ (123 mg, 0.90 mmol) in anhydrous DMF (20 mL) was stirred at room temperature for 12 h. The reaction mixture was diluted with EtOAc (20 mL), washed with $H_2O$ (2×20 mL), brine (2×10 mL), dried over $Na_2SO_4$ and evaporated under reduced pressure to yield a crude product. The crude was purified by column chromatography (petroleum ether/EtOAc; 1:1) to yield 190 mg (94%) of TD-9 as a yellow-colored solid: mp 104-105° C.; IR (KBr, cm$^{-1}$): 3153 (0-H), 1599 (C=O); $^1$H-NMR (CDCl$_3$): δ 3.58 (s, 1H, OH), 3.85 (s, 3H, OCH$_3$), 4.78 (d, 2H, CH$_2$), 5.30 (s, 2H, CH$_2$), 6.53 (d, J=2.2 Hz, 1H, ArH), 6.60 (d, J=2.16 Hz, 1H, ArH), 7.22 (d, J=7.68 Hz, 2H, ArH), 7.47 (d, J=7.76 Hz, 2H, ArH), 7.76 (t, 1H, ArH), 7.85 (d, J=8.64 Hz, 1H, ArH), 10.43 (s, 1H, CHO); $^{13}$C-NMR (CDCl$_3$): δ 166.16, 162.27, 158.67, 155.51, 137.74, 131.04, 119.85, 119.69, 118.1, 106.68, 99.16, 70.85, 63.87, 55.66. MS (ESI) m/z found 274.11 (M+H)$^+$, 296.09 (M+Na)$^+$. The purity of the compound was checked by HPLC and was found to be 96.9% pure.

Synthesis Example 4

3-((6-(Hydroxymethyl)pyridine-2-yl)methoxy)-4-methoxybenzaldehyde (TD-8)

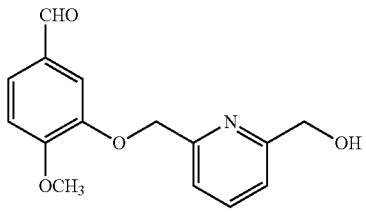 [SMILES: COc1ccc(C=O)cc1OCc1cccc(CO)n1]

Compound TD-8 was prepared according to literature procedure for a similar compound. (Nnamani, I. N.; Joshi, G. S.; Danso-Danquah, R.; Abdulmalik, O.; Asakura, T.; Abraham, D. J.; Safo, M. K., *Chem. Biodivers.* 2008, 5, 1762-1769.)

A mixture of 3-hydroxy-4-methoxybenzaldehyde (200 mg, 1.0 mmol), 6-(bromomethyl)-2-pyridinemethanol (152 mg, 1.0 mmol), and potassium carbonate (165 mg, 1.2 mmol) in anhydrous DMF (20 mL) was stirred at room temperature for 12 h. The reaction mixture was diluted with EtOAc (20 mL), washed with $H_2O$ (2×20 mL), brine (2×10 mL), dried over $Na_2SO_4$ and evaporated under reduced pressure to yield a crude product. The crude product was purified by column chromatography (petroleum ether/EtOAc; 1:1) to yield 220 mg (80%) of TD-8 as a white-colored solid: mp 120-121° C.; IR (KBr, cm$^{-1}$): 3176 (0-H), 1681 (C=O); $^1$H-NMR (CDCl$_3$): δ 3.65 (s, 1H, OH), 4.00 (s, 3H, OCH$_3$), 4.78 (d, 2H, CH$_2$), 5.32 (d, 2H, CH$_2$), 7.03 (d, J=8.72 Hz, 1H, ArH), 7.17 (d, J=7.68 Hz, 1H, ArH), 7.44-7.51 (m, 3H, ArH), 7.71 (t, 1H, ArH); $^{13}$C-NMR (CDCl$_3$): δ 190.66, 155.53, 154.95, 137.54, 130.11, 126.88, 119.99, 119.60, 111.92, 110.98, 158.79, 71.40, 63.90, 56.22. MS (ESI) m/z found 274.11 (M+H)$^+$, 296.09 (M+Na)$^+$. The purity of the compound was checked by HPLC and was found to be 99.5% pure.

Synthesis Example 5

(6-((2-Formyl-4-methoxyphenoxy)methyl)pyridin-2-yl)methyl nitrate (TD-7-1)

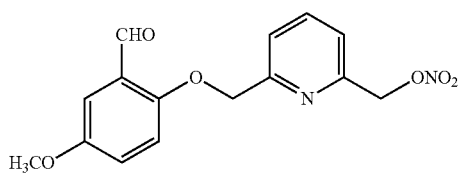

Compound TD-7-1 was prepared according to literature procedure for a similar compound. (Fotopoulou, T.; Iliodromitis, E. K.; Koufaki, M.; Tsotinis, A.; Zoga, A.; Gizas, V.; Pyriochou, A.; Papapetropoulos, A.; Andreadou, I.; Kremastinos, D. T., *Bioorg. Med. Chem.* 2008, 16, 4523-4531.)

Silver nitrate (76 mg, 0.45 mmol) was added to a solution of 2-((6-(bromomethyl)pyridin-2-yl)methoxy)-5-methoxybenzaldehyde (100 mg, 0.3 mmol) in anhydrous $CH_3CN$ (5 mL). The reaction mixture was allowed to stir at 80° C. for 2 h. The reaction mixture was filtered through celite and washed with $CH_2Cl_2$ (15 mL), and evaporated under reduced pressure to yield a crude product. The crude residue was purified by column chromatography (petroleum ether/EtOAc; 5:1) to yield 80 mg (83.78%) of TD-7-1 as a white-colored solid: mp 92-93° C.; IR (KBr, $cm^{-1}$): 1664 (C=O), 1632 ($NO_2$), 1274 ($NO_2$), 872 (ON); $^1$H-NMR ($CDCl_3$): δ 3.81 (s, 3H, $OCH_3$), 5.28 (d, 2H, $CH_2$), 5.56 (s, 2H, $CH_2$), 6.98 (d, J=9.08 Hz, 1H, ArH), 7.10-7.13 (dd, J=9.08, 3.28 Hz, 1H, ArH), 7.33-7.37 (dd, J=8.4, 3.24 Hz, 2H, ArH), 7.53 (d, J=7.84 Hz, 1H, ArH), 7.80 (t, 1H, ArH), 10.57 (s, 1H, CHO); $^{13}$C-NMR ($CDCl_3$): δ 189.18, 157.08, 155.20, 154.20, 152.50, 138.05, 125.52, 123.38, 121.27, 121.19, 114.85, 111.00, 74.15, 71.51, 55.85. MS (ESI) m/z found 319.09 $(M+H)^+$, 341.07 $(M+Na)^+$. The purity of the compound was checked by HPLC and was found to be 94.5% pure.

Synthesis Example 6

2-((6-(Bromomethyl)pyridin-2-yl)methoxy)-5-methoxybenzaldehyde

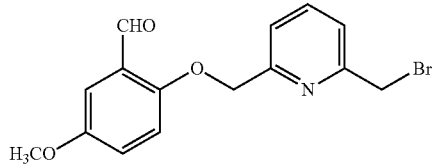 [SMILES: COc1ccc(OCc2cccc(CBr)n2)c(C=O)c1]

2-((6-(Bromomethyl)pyridin-2-yl)methoxy)-5-methoxybenzaldehyde, a precursor for the synthesis of TD-7-1 was prepared according to literature procedure for a similar procedure. (Fotopoulou, T.; Iliodromitis, E. K.; Koufaki, M.; Tsotinis, A.; Zoga, A.; Gizas, V.; Pyriochou, A.; Papapetropoulos, A.; Andreadou, 1.; Kremastinos, D. T., *Bioorg. Med. Chem.* 2008, 16, 4523-4531.). Triphenylphosphine (140 mg, 0.6 mmol) and tetrabromomethane (180 mg, 0.6 mmol) was added to a solution of 2-((6-(hydroxymethyl)pyridin-2-yl)methoxy)-5-methoxybenzaldehyde (100 mg, 0.4 mmol) in anhydrous $CH_2Cl_2$ (6 mL). The reaction mixture was allowed to stir for 2 h at room temperature. The reaction mixture was neutralized with saturated $NaHCO_3$ at 0° C. (ice-bath) and extracted with EtOAc (10 mL). The organic portion was washed with brine (2×10 mL), dried over $Na_2SO_4$ and evaporated under reduced pressure to yield a crude product. The crude was purified by column chromatography (petroleum ether/EtOAc; 5:1) to yield 100 mg (74.6%) as a yellow-colored solid: $^1$H-NMR ($CDCl_3$): δ 3.81 (s, 3H, $OCH_3$), 4.56 (s, 2H, $CH_2$), 5.28 (d, 2H, $CH_2$), 6.98 (d, J=9.08 Hz, 1H, ArH), 7.10-7.13 (dd, J=9.08, 3.28 Hz, 1H, ArH), 7.33-7.37 (dd, J=8.4, 3.24 Hz, 2H, ArH), 7.53 (d, J=7.84 Hz, 1H, ArH), 7.80 (t, 1H, ArH), 10.58 (s, 1H, CHO). The following compound was used for the synthesis of TD-7-1.

Synthesis Example 7

(6-((5-Formyl-2-methoxyphenoxy)methyl)pyridin-2-yl)methyl nitrate (TD-8-1)

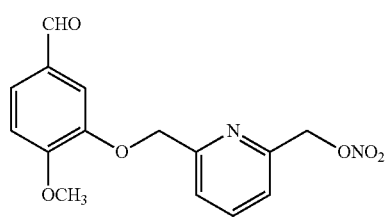

Compound TD-8-1 was prepared according to literature procedure for a similar compound. (Fotopoulou, T.; Iliodromitis, E. K.; Koufaki, M.; Tsotinis, A.; Zoga, A.; Gizas, V.; Pyriochou, A.; Papapetropoulos, A.; Andreadou, I.; Kremastinos, D. T., *Bioorg. Med. Chem.* 2008, 16, 4523-4531.). Silver nitrate (76 mg, 0.45 mmol) was added to a solution of 3-((6-(bromomethyl)pyridine-2-yl)methoxy)-4-methoxybenzaldehyde (100 mg, 0.3 mmol) in anhydrous $CH_3CN$ (5 mL). The reaction mixture was allowed to stir at 80° C. for 2 h. The reaction mixture was filtered through celite and washed with $CH_2Cl_2$ (15 mL) and evaporated under reduced pressure to yield a crude product. The crude was purified by column chromatography (petroleum ether/EtOAc; 5:1) to yield 94 mg (98%) of TD-8-1 as a yellow-colored solid: mp 43-44° C.; IR (KBr, $cm^{-1}$): 1683 (C=O), 1632 ($NO_2$), 850 (ON); $^1$H-NMR ($CDCl_3$): δ 3.99 (s, 3H, $OCH_3$), 5.31 (s, 2H, $CH_2$), 5.57 (s, 2H, $CH_2$), 7.02 (d, J=8.24 Hz, 1H, ArH), 7.31 (d, J=7.68 Hz, 1H, ArH), 7.46 (d, J=2.16 Hz, 1H, ArH), 7.49-7.52 (dd, J=8.2, 1.76 Hz, 1H, ArH), 7.55 (d, J=7.76 Hz, 1H, ArH), 9.82 (s, 1H, CHO); $^{13}$C-NMR ($CDCl_3$): δ 190.56, 157.157, 155.01, 152.01, 152.47, 148.42, 137.91, 130.20, 126.78, 121.34, 121.00, 112.24, 111.08, 74.27, 71.43, 56.24. MS (ESI) m/z found 341.08 $(M+Na)^+$. The purity of the compound was checked by HPLC and was found to be 96.9% pure.

Synthesis Example 8

3-((6-(Bromomethyl)pyridine-2-yl)methoxy)-4-methoxybenzaldehyde

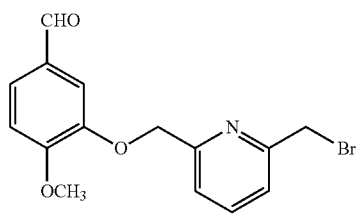 [SMILES: COc1ccc(C=O)cc1OCc1cccc(CBr)n1]

3-((6-(Bromomethyl)pyridine-2-yl)methoxy)-4-methoxybenzaldehyde, a precursor for the synthesis of TD-8-1 was prepared according to literature procedure for a similar procedure. (Fotopoulou, T.; Iliodromitis, E. K.; Koufaki, M.; Tsotinis, A.; Zoga, A.; Gizas, V.; Pyriochou, A.; Papapetropoulos, A.; Andreadou, I.; Kremastinos, D. T., *Bioorg. Med. Chem.* 2008, 16, 4523-4531.). Triphenylphosphine (140 mg, 0.6 mmol) and tetrabromomethane (180 mg, 0.6 mmol) was added to a solution of 3-((6-(hydroxymethyl)pyridine-2-yl)methoxy)-4-methoxybenzaldehyde (100 mg, 0.4 mmol in anhydrous $CH_2Cl_2$ (6 mL). The mixture was allowed to stir for 2 h at room temperature. The reaction mixture was neutralized with saturated $NaHCO_3$ at 0° C. (ice-bath) and extracted with EtOAc (10 mL). The organic portion was washed with brine (2×10 mL), dried over $Na_2SO_4$ and evaporated under reduced pressure to yield a crude product. The crude was purified by column chromatography (petroleum ether/EtOAc; 5:1) to yield 76 mg (56.5%) as a yellow-colored solid: $^1$H-NMR ($CDCl_3$-$d_1$): δ 3.99 (s, 3H, $OCH_3$), 4.56 (s, 2H, $CH_2$), 5.31 (s, 2H, $CH_2$), 7.02 (d, 0.1=8.2 Hz, 1H, ArH), 7.38 (d, J=7.8 Hz, 1H, ArH), 7.46 (d, J=7.8 Hz, 1H, ArH), 7.49 (d, J=1.84 Hz, 1H, ArH), 7.52 (d, J=1.76 Hz, 1H, ArH), 7.72 (t, 1H, ArH), 9.82 (s, 1H, CHO). The following compound was used for the synthesis of TD-8-1.

Synthesis Example 9

(6-((2-Formyl-5-methoxyphenoxy)methyl)pyridin-2-yl)methyl nitrate (TD-9-1)

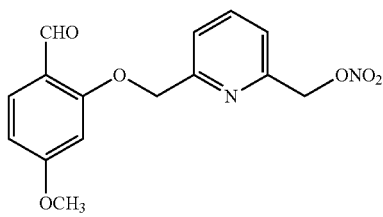

Compound TD-9-1 was prepared according to literature procedure for a similar compound. (Fotopoulou, T.; Iliodromitis, E. K.; Koufaki, M.; Tsotinis, A.; Zoga, A.; Gizas, V.; Pyriochou, A.; Papapetropoulos, A.; Andreadou, 1.; Kremastinos, D. T., *Bioorg. Med. Chem.* 2008, 16, 4523-4531.).

Silver nitrate (76 mg, 0.5 mmol) was added to a solution of 2-((6-(bromomethyl)pyridin-2-yl)methoxy)-4-methoxybenzaldehyde (100 mg, 0.3 mmol) in anhydrous $CH_3CN$ (5 mL). The reaction mixture was allowed to stir at 80° C. for 2 h. The reaction mixture was filtered through celite and washed with $CH_2Cl_2$ (15 mL) and evaporated under reduced pressure to yield a crude product. The crude product was purified by column chromatography (petroleum ether/EtOAc; 5:1) to yield 53 mg (56%) of TD-9-1 as a white-colored solid: mp 70-71° C.; IR (KBr, $cm^{-1}$): 1677 (C=O), 1285 ($NO_2$), 871 (ON); $^1$H-NMR ($CDCl_3$-$d_1$): δ 3.85 (s, 3H, $OCH_3$), 5.29 (s, 2H, $CH_2$), 5.56 (s, 2H, $CH_2$), 6.52 (d, J=2.16 Hz, 1H, ArH), 6.58-6.61 (m, 1H, ArH), 7.34 (d, J=7.68 Hz, 1H, ArH), 7.58 (d, J=7.88 Hz, 1H, ArH), 7.79-7.85 (m, 2H, ArH), 10.42 (s, 1H, CHO); $^{13}$C-NMR ($CDCl_3$): δ 166.19, 163.05, 158.71, 155.53, 138.15, 131.18, 121.31, 121.28, 118.15, 106.95, 99.07, 74.14, 70.80, 55.68. MS (ESI) m/z found 341.08 $(M+Na)^+$. The purity of the compound was checked by HPLC and was found to be 99.8% pure.

2((6-(Bromomethyl)pyridin-2-yl)methoxy)-4-methoxybenzaldehyde

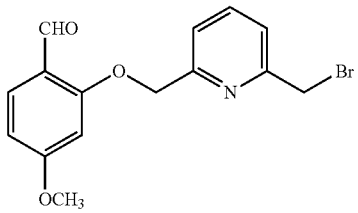 [SMILES: COc1ccc(C=O)c(OCc2cccc(CBr)n2)c1]

2-((6-(Bromomethyl)pyridin-2-yl)methoxy)-4-methoxybenzaldehyde, a precursor for the synthesis of TD-9-1 was prepared according to literature procedure for a similar procedure. (Fotopoulou, T.; Iliodromitis, E. K.; Koufaki, M.; Tsotinis, A.; Zoga, A.; Gizas, V.; Pyriochou, A.; Papapetropoulos, A.; Andreadou, I.; Kremastinos, D. T., *Bioorg. Med. Chem.* 2008, 16, 4523-4531.)

Triphenylphosphine (140 mg, 0.6 mmol) and tetrabromomethane (180 mg, 0.6 mmol) was added to a solution of 2-((6-(hydroxymethyl)pyridin-2-yl)methoxy)-4-methoxybenzaldehyde (100 mg, 0.4 mmol) in anhydrous $CH_2Cl_2$ (6 mL). The mixture was allowed to stir for 2 h at room temperature. The reaction mixture was neutralized with saturated $NaHCO_3$ at 0° C. (ice-bath) and extracted with EtOAc (10 mL). The organic portion was washed with brine (2×10 mL), dried over $Na_2SO_4$ and evaporated under reduced pressure to yield a crude product. The product was purified by column chromatography (petroleum ether/EtOAc; 5:1) to yield 100 mg (75%) as a yellow-colored solid: $^1$H-NMR ($CDCl_3$): δ 3.85 (s, 3H, $OCH_3$), 4.56 (s, 2H, $CH_2$), 5.30 (s, 2H, $CH_2$), 6.53 (d, J=2.16 Hz, 1H, ArH), 6.57-6.59 (m, 1H, ArH), 7.40 (d, J=7.72 Hz, 1H, ArH), 7.50 (d, J=7.8 Hz, 1H, ArH), 7.76 (t, 1H, ArH), 7.84 (t, J=8.68 Hz, 1H, ArH), 10.43 (s, 1H, CHO). The resulting compound was used for the synthesis of TD-9-1.

Synthesis Example 10

TD-7 Hydrochloric Salt

A solution of 1.0 M HCl (5 mL) in diethyl ether was added in a drop-wise fashion to a stirring solution of TD-7 (200 mg) in absolute ethanol (3 mL), resulting in precipitation of the hydrochloride salt of TD-7. Ethyl ether (10 mL) was added to the mixture to completely precipitate all the HCl salt. The compound was filtered by vacuum filtration, washed with more ether and further dried under vacuum. The yield obtained was 88%.

Biological Example 1

Oxygen Equilibrium Curve (OEC) Studies

Studies were performed on compounds TD-7, TD-7-1, TD-8, TD-8-1, TD-9 and TD-9-1 using 100 mM stock solution in DMSO and normal whole blood (AA). TD-7, TD-8 and TD-9 are compounds with a hydroxymethyl group on the pyridine ring, while TD-7-1, TD-8-1 and TD-9-1 are the respective nitrate ester derivatives. The whole blood samples had hematocrit values ranging from 29-36%, and cell-free purified Hb of 10-12 g/dL in the absence or presence of effectors solubilized in DMSO at 2 mM or in some cases with varying compound concentration. The blood samples were incubated in an IL 237 tonometer (Instrumentation Laboratories, Inc., Lexington, Mass.) for about 5-7 min at 37° C. against a gas mixture containing $O_2$ concentrations of 0.804%, 2.935% and 5.528% and allowed to equilibrate at $O_2$ tensions of 6, 20 and 40 mmHg. After equilibration, the sample was removed via syringe and aspirated into a ABL 700 series table top automated blood gas analyzer (Radiometer America, Inc., Westlake, Ohio) to determine total hemoglobin (tHb), hematocrit (Hct), pH, $pCO_2$, partial pressure of oxygen ($pO_2$), and the Hb oxygen saturation values ($sO_2$). Similar procedures were followed for concentration and time dependence studies. The measured values of $pO_2$ and $sO_2$ at each oxygen saturation level were then subjected to a non-linear regression analysis using the program Scientist (*Micromath*, Salt Lake City, Utah) with the following equation:

$$sO_2\% = 100 \times \frac{pO_2^N \text{mmHg}}{P_{50}^N(\text{mmHg}) + pO_2^N(\text{mmHg})}$$

This equation was used to calculate $P_{50}$ and Hill coefficient (N) values. Corresponding control experiments without the test compound ($P_{50control}$) but containing DMSO were also performed. 5HMF is known to exhibit optimal left-shifting activity between 1 to 2 h when incubated with whole blood necessitating the use of 1.5 h for the incubation time for our studies. The results are shown in Table 1 and FIG. 1. The most potent left-shifter was TD-7 with a $\Delta P_{50}$ shift of −17.0 mmHg, more potent than the positive control, 5HMF ($\Delta P_{50}$ of −11.1 mmHg).

TABLE 1

Effects of left-shifting compounds on Hb affinity for $O_2$ with normal whole blood.

| Compound | Concentration (mM) | $P_{50}$ (mmHg) | $N^a$ | $\Delta P_{50}^b$ (mmHg) |
| --- | --- | --- | --- | --- |
| 5HMF | 2 | 20.2 ± 2.0$^{c\dagger}$ | 1.8 ± 0.1$^{c\dagger}$ | −11.1 |
| TD-7 | 0.1 | 30.1$^{d*}$ | 2.5$^{d*}$ | −0.5 |
|  | 0.5 | 25.9$^{d*}$ | 2.1$^{d*}$ | −4.7 |
|  | 1 | 23.2$^{d*}$ | 1.7$^{d*}$ | −7.4 |
|  | 2 | 14.3 ± 4.3$^{c\dagger}$ | 1.3 ± 0.3$^{c\dagger}$ | −17.0 |
| TD-8 | 2 | 25.9 ± 2.5$^{c\dagger}$ | 1.9 ± 0.1$^{c\dagger}$ | −5.4 |
| TD-9 | 2 | 21.1 ± 1.2$^{c\dagger}$ | 1.6 ± 0.3$^{c\dagger}$ | −10.2 |
| TD-1 | 2 | 27.4 ± 2.3$^{c\dagger}$ | 1.9 ± 0.1$^{c\dagger}$ | −3.9 |
| TD-7-1 | 2 | 23.4 ± 1.6$^{c\dagger}$ | 1.7 ± 0.1$^{c\dagger}$ | −7.9 |
| TD-8-1 | 2 | 30.8$^{d\dagger}$ | 2.1$^{d\dagger}$ | −0.5 |
| TD-9-1 | 2 | 28.6$^{d\dagger}$ | 1.9$^{d\dagger}$ | −2.7 |

$^a$Hill coefficient;
$^b\Delta P_{50}$ is ($P_{50}$ (control)-$P_{50}$ (sample)) expressed in mmHg;
$^c$measurements were conducted in n ≥ 3;
$^d$measurements were conducted in n < 3

Biological Example 2

Blood Collection and Purification of Hemoglobin

Hemoglobin was prepared from centrifuging human blood at 2500 rpms for 20 min at 4° C. The supernatant solution, debris and plasma were discarded from the centrifuge bottles, leaving behind RBCs. The RBCs were washed thrice with an excess volume of 0.9% NaCl, and once with 1.0% NaCl, each time centrifuging and discarding the supernatant solution. The RBCs were pooled together into a chilled flask and hemolyzed to free Hb by adding 1-2 volume excess of 50 mM Tris buffer, pH 8.6 (containing EDTA). The mixture was allowed to stand in ice for 30 min with occasional stirring. The Hb solution was centrifuged at 10,000 rpm for 2 h at 4° C. The supernatant Hb solution was pooled into a chilled flask and NaCl (40-60 mg/mL Hb solution) was slowly added with stirring. Hemoglobin solution was centrifuged at 10,000 rpm for 2 h at 4° C. to remove any cell stroma remnants. The clear supernatant Hb solution was pooled into a chilled flask and the "syrupy" pellet was discarded. Hemoglobin solution was dialyzed against 50 mM Tris buffer, pH 8.6 (containing EDTA) at 4° C. to remove NaCl and/or other low molecular weight impurities. Strips of standard cellulose dialysis tubing that had been washed 3-4 times and boiled for 10 min in deionized water were used for dialysis. The dialyzed Hb was further purified by ion-exchange chromatography using DEAE sephacel to exclude 2,3-DPG. The resin was equilibrated with 50 mM Tris buffer, pH 8.6, and the Hb solution was run through the column with 50 mM Tris buffer, pH 8.6 (containing EDTA). The pooled fractions were concentrated with an Amicon stirred cell (Amicon, Model 402), to a final HbA concentration of about 80-120 mg/mL. Concentrated HbA was stored at −80° C.

Biological Example 3

OEC Study with Compounds TD-1, TD-7, TD-7-1, TD-8 and TD-9 with Normal Cell-Free Hb As a result of the low left-shifting activities of TD-8 and TD-9, as well as the nitrate ester derivatives, we further evaluated the activity of the compounds TD-1, TD-7, TD-7-1, TD-8, and TD-9 using cell-free Hb (devoid of any proteins, enzymes, plasma and cell membranes) to determine whether plasma protein or RBC membrane could have any effect on compound biological activity. Previous studies have shown limited effect of plasma protein and RBC membrane on SHMF activity. The same tonometry procedure used on whole blood was used with the cell-free hemoglobin using 2 mM compound and 12 mg/mL of Hb. The results are shown in Table 2.

TABLE 2

Effects of left-shifting compounds on Hb affinity for $O_2$ with cell-free Hb.

| Compound | $P_{50}$ (mmHg) | $N^a$ | $\Delta P_{50}^b$ (mmHg) |
| --- | --- | --- | --- |
| Control | 12.5 | 2.6 | — |
| 5HMF | 8.3 | 2.0 | −4.2 |
| TD-7 | 7.6 | 1.8 | −4.9 |
| TD-8 | 7.6 | 1.9 | −4.9 |
| TD-9 | 6.8 | 1.7 | −5.7 |
| TD-1 | 8.4 | 2.0 | −4.1 |
| TD-7-1 | 7.7 | 2.1 | −3.9 |

$^a$Hill coefficient;
$^b\Delta P_{50}$ is ($P_{50}$ (control)-$P_{50}$ (sample)) expressed in mmHg;
measurements were conducted in n = 1.

Unlike the results obtained from the whole blood study (Table 1), the results depicted in Table 2 show that all compounds exhibit significant left-shift in the OEC with cell-free Hb. TD-8 which barely shifted the OEC with whole blood now shows comparable shift as TD-7 with cell-free Hb. Also, TD-9 appears to be an even more potent left-shifter in cell-free Hb than TD-7, which was opposite to what was observed with whole blood. Although the nitrate esters still show less left-shift compared to the parent compounds, there is still significant improvement in their left-shifting potency with cell-free Hb. This observation suggests that the functional activities of both TD-8 and TD-9 are significantly affected by RBC membrane permeability issues and/or plasma protein binding resulting in their reduced allosteric activities.

Biological Example 4

Time-Dependent OEC Studies with TD-7

This study shows time-dependent left-shifting effect of TD-7 compared to 5HMF. All samples were pre-incubated with whole blood (Hct~34%) with the specified compounds 0.5 mM concentrations for the specified time. The control experiment without test compound ($P_{50}$ (control)) contains the same concentration of DMSO used to solubilize the test solution ($P_{50}$ (sample)). The results are shown in Table 3 and FIG. 2.

TABLE 3

Effect of incubation time on Hb affinity for $O_2$ with whole blood for left-shifting compounds.

| Compound | Incubation Time (Hours) | $P_{50}$ (mmHg) | $N^a$ | $\Delta P_{50}{}^b$ (mmHg) |
|---|---|---|---|---|
| Control | 1 | 32.7 ± 0.2 | 2.5 ± 0.1 | — |
|  | 2 | 33.0 ± 0.4 | 2.5 ± 0.1 | — |
|  | 4 | 33.1 ± 0.6 | 2.5 ± 0.1 | — |
|  | 6 | 34.2 ± 0.3 | 2.5 ± 0.1 | — |
|  | 10 | 35.1 ± 0.3 | 2.5 ± 0.1 | — |
|  | 12 | 36.1 ± 0.4 | 2.4 ± 0.1 | — |
| 5HMF | 1 | 29.8 ± 0.2 | 2.2 ± 0.1 | −2.9 |
|  | 2 | 29.2 ± 0.3 | 2.2 ± 0.1 | −3.8 |
|  | 4 | 29.2 ± 0.1 | 2.1 ± 0.1 | −3.9 |
|  | 6 | 30.0 ± 0.1 | 2.1 ± 0.1 | −4.2 |
|  | 10 | 31.8 ± 0.1 | 2.1 ± 0.1 | −3.3 |
|  | 12 | 32.8 ± 0.1 | 2.0 ± 0.1 | −3.3 |

| Compound | Incubation Time (Hours) | $P_{50}$ (mmHg) | N | $\Delta P_{50}$ (mmHg) |
|---|---|---|---|---|
| TD-7 | 1 | 28.2 ± 0.9 | 2.2 ± 0.2 | −4.5 |
|  | 2 | 28.2 ± 0.8 | 2.1 ± 0.1 | −4.8 |
|  | 4 | 28.8 ± 0.6 | 2.1 ± 0.1 | −4.3 |
|  | 6 | 29.1 ± 0.6 | 2.0 ± 0.2 | −5.1 |
|  | 10 | 30.6 ± 1.0 | 2.0 ± 0.1 | −4.5 |
|  | 12 | 31.1 ± 0.7 | 2.0 ± 0.2 | −5.0 |

Figure 2:
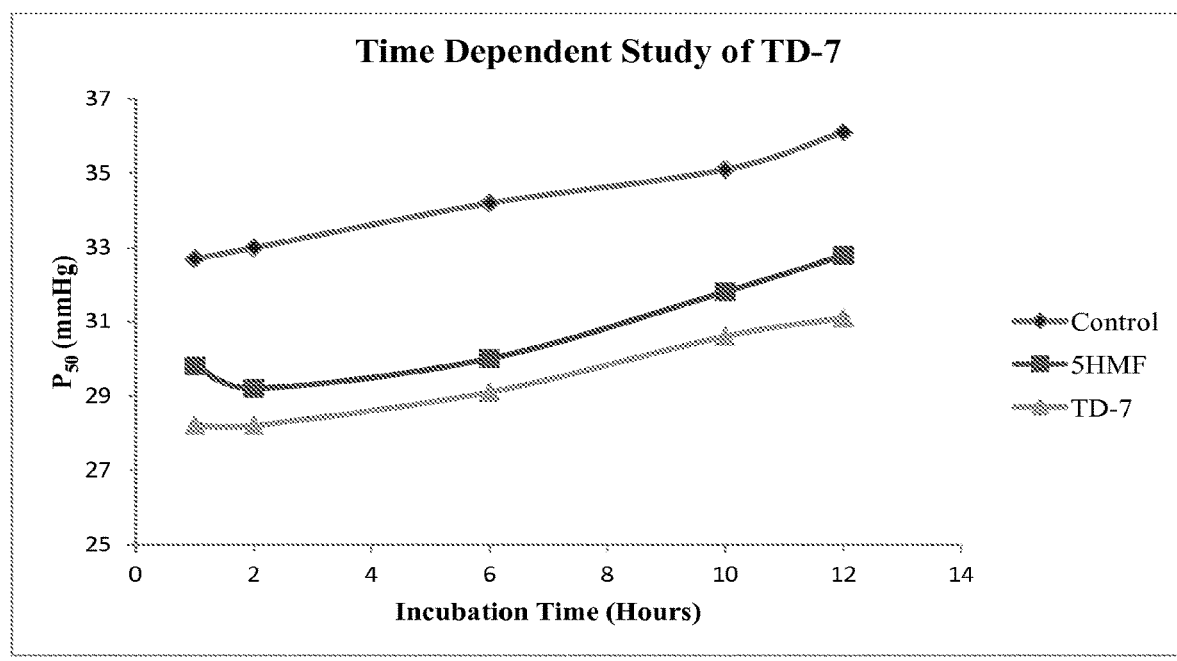
FIG. 2 shows the effect of incubation time on Hb affinity for O$_2$ with whole blood for 5-HMF and compound TD-7.

$^a$Hill coefficient;
$^b\Delta P_{50}$ is ($P_{50}$ (control)-$P_{50}$ (sample)) expressed in mmHg;
$^c$measurements were conducted in n ≥ 3;.
The $P_{50}$ values of control were found to increase consistently, with incubation.
While the $P_{50}$ values for 5HMF seem to return to baseline after 6 h, there was no recovery for TD-7 even after 12 h suggesting TD-7 will have a longer sustained effect (FIG. 2).

Biological Example 5

NO Release Study for Compounds TD-1, TD-7-1, TD-8-1 and TD-9-1

Figure 3:
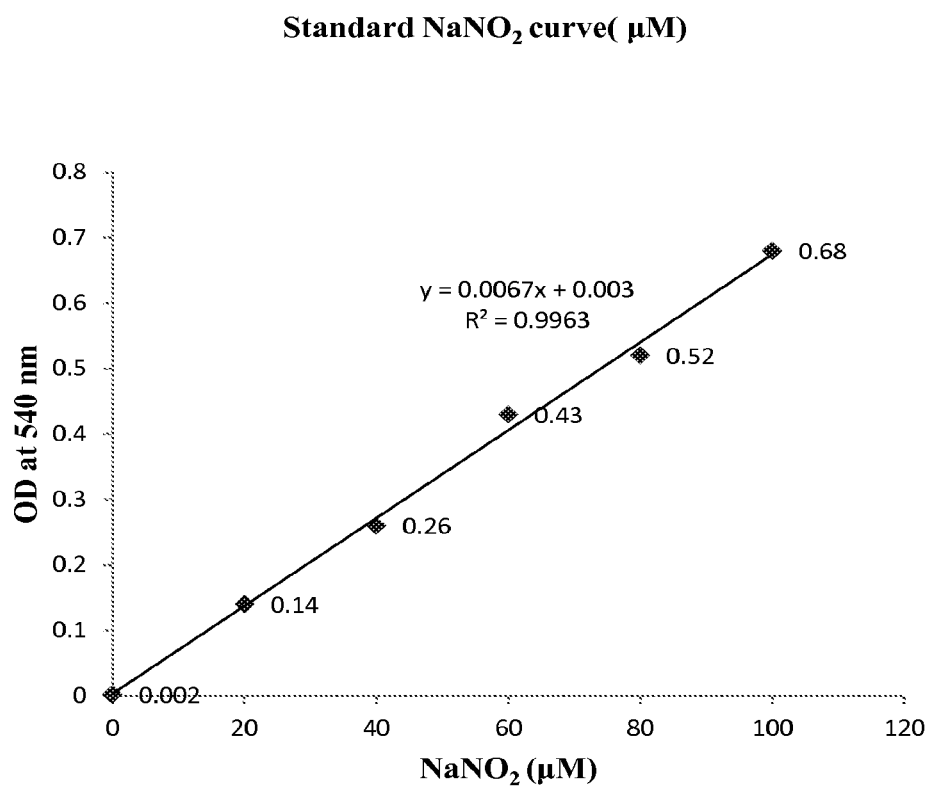
FIG. 3 shows results of a NO release study for compounds TD-1, TD-7-1, TD-8-1 and TD-9-1.

Griess assay was performed on the left-shifting nitrate ester compounds (TD-1, TD-74, TD-8-1 and, TD-9-1) to measure the release of NO. Griess assay is a colorimetric assay, used for detection of NO in the form of nitrite ions ($NO_2^-$). NO released in solution is highly unstable, with a half-life of 1 to 30 s. It gets rapidly oxidized to $NO_2^-$ which is detected by the Griess reagent. In this method, $NO_2^-$, first reacts with the sulfanilamide present in the reagent to form a transient diazonium salt. This diazonium salt further reacts with N-naphthyl-ethylenediamine (NED) to form a stable azo compound which possesses an intense purple color. The absorbance of the azo compound was measured at 540 urn and was found to be directly proportional to the NOT concentration in the sample. Sodium nitrite ($NaNO_2$) was used as a standard for the Griess assay. $NaNO_2$ samples in deionized water were prepared of concentrations within the linear range of the assay (1-100 μM). The samples were incubated for 30 min at 37° C., after which Griess reagent was added and absorbance was measured at 540 nm. The measured absorbances were used to obtain a standard curve (FIG. 3). For the measurement of $NO_2^-$ release for all the test compounds (TD-1, TD-7-1, TD-8-1 and TD-9-1), the absorbances were extrapolated from the standard $NaNO_2$ curve.

In this assay, a solution of the test compound (1 mL of a 2 mM solution in 0.1 M phosphate buffer (pH 7.4)) was mixed thoroughly with a freshly prepared solution of L-cysteine (1 mL of a 36 mM solution in 0.1 M phosphate buffer, pH 7.4), and incubated at 37° C., for 1 and 16 h under anaerobic conditions. After exposure to air for 10 min at 25° C., an aliquot of the Griess reagent (1 mL) [freshly prepared by mixing equal volumes of 1.0% sulfanilamide (prepared and stored in aqueous 5% phosphoric acid) and 0.1% N-naphthylethylenediamine dihydrochloride in water] was added to an equal volume (1 mL) of each incubation solution after mixing. After 10 min, absorbance was measured at 540 nm using a Hewlett Packard (Agilent) 8453 UV-visible Spectroscopy. $NaNO_2$ solutions of 1-100 μM concentrations were used to prepare a standard nitrite curve of absorbance (nm) versus concentration (μM). The NO released (quantitated as $NO_2^-$ release in μM) was calculated from the standard nitrite curve by extrapolation of the absorbance. Presence of $NO_2^-$ shows formation of a pink color, the intensity of which is directly proportional to the amount of $NO_2^-$ present in the mixture. Table 4 represents $NO_2^-$ release for compounds TD-1, TD-7-1, TD-8-1 and TD-9-1.

TABLE 4

Absorbance and $NO_2^-$ release values for Compounds TD-1, TD-7-1, TD-8-1 and TD-9-1.

| Incubation Time (Hours) | $NO_2^-$ release$^a$ (μM) after 1 hour | $NO_2^-$ release$^a$ (μM) after 16 hours |
|---|---|---|
| TD-1 | 4.02 | 11.93 |
| TD-7-1 | 7.61 | 59.25 |
| TD-8-1 | 21.94 | 102.54 |
| TD-9-1 | 20.45 | 78.66 |

$^a$The $NO_2^-$ release (μM) was calculated from the standard $NaNO_2$ curve by extrapolating the absorbance (nm) of the test compounds against the concentration (μM) of $NaNO_2$.

All four compounds (TD-1, TD-7-1, TD-8-1 and TD-9-1) exhibited significant nitric oxide release (4.0-21.9 μM range at 1 h and 59-102.5 μM range at 16 h) upon incubation in the presence of L-cysteine. The NO release after 16 h incubation was found to be 3-10 fold higher than 1 h incubation. From Table 4, it can be interpreted that for all the compounds, the NO release in the form of $NO_2^-$ is found to increase with time, with TD-1 showing the least release, while TD-8-1 showed the most release.

Biological Example 6

In Vitro RBC Anti-Sickling Studies with Compounds 5HMF, TD-1, TD-7 and TD-7-1

In vitro RBC morphological (anti-sickling) analysis was conducted at the Children's Hospital of Philadelphia (by Drs. Toshio Asakura and Osheiza Abdulmalik). The antisickling effects of 5HMF, TD-7 HCl, TD-7, TD-1, and TD-7-1 were studied by incubating suspensions of SS cells in the absence or presence of three different concentrations of the effectors in the presence of air for 1 h at 37° C. followed by incubation under 4% oxygen at 37° C. for 5 h. All samples were pre-incubated for 1 h with various compounds and then incubated under 4% $O_2$ for 5 h. Hb had a hematocrit of 30%. Table 5 represents the concentrations of the effectors along with the % inhibition of sickling cells. The hemolysates that had been prepared from SS cells after incubation with test compounds were also subjected to cation-exchange HPLC as previously reported (Abdulmalik et al., 2005). Table 5 shows the effect of the various concentrations of the test compounds on the amount of modified Hb S which reflects Schiff-base adduct formation between the aromatic aldehyde and the protein.

TABLE 5

Effects of various concentrations of compounds on inhibition of SS cell sickling.

| Compound | Concentration (mM) | Inhibition of sickled cells (%) |
|---|---|---|
| 5HMF | 0.5 | 4 |
|  | 1.0 | 17 |
|  | 2.0 | 35 |
|  | 5.0 | 75 |
| TD-7 HCl salt | 1.0 | 100 |
|  | 2.0 | 100 |
|  | 5.0 | 100 |
| TD-7 | 0.5 | 95 |
|  | 1.0 | 95 |
|  | 2.0 | 100 |
|  | 5.0 | 100 |
| TD-8 | 0.5 | 14 |
|  | 1.0 | 20 |
|  | 2.0 | 38 |
| TD-9 | 0.5 | 26 |
|  | 1.0 | 35 |
|  | 2.0 | 57 |
| TD-7-1 | 0.5 | 72 |
|  | 1.0 | 100 |
|  | 2.0 | 100 |

Figure 4:
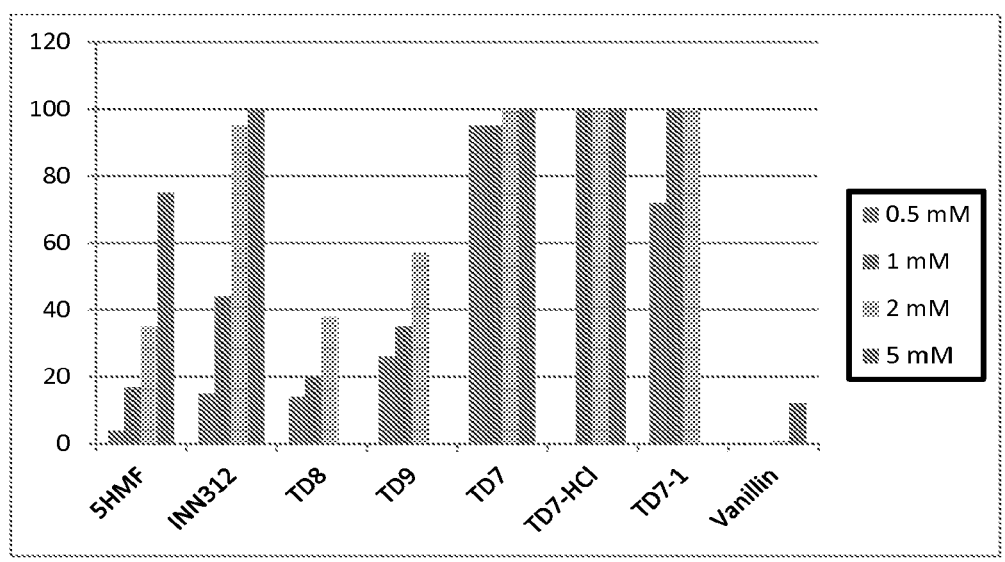
FIG. 4 shows inhibition of sickling of SS cells by test compounds under 4% O$_2$ at 37° C. for 5 h.

The anti-sickling effects of 5HMF, TD-7, TD-7 HCl salt, TD-1, and TD-7-1 were studied and the results shown in Table 5 and FIG. 4 (% inhibition). In the absence of test compounds, about 95% of the Hb underwent sickling in 5 h. In the presence of the positive control, 5HMF, the percentage of the sickled cells decreased in a dose-dependent manner with 4, 17, 35 and 75% inhibition at 0.5 mM, 1 mM, 2 mM and 5 mM concentration, respectively. In comparison, TD-1, the nitrate ester analog of 5HMF showed only a modest decrease in the anti-sickling effect (Not shown in Table). This observation may be partly related to poor RBC membrane passage. Remarkably TD-7, either the free base or HCl salt, showed a very potent anti-sickling effect, as much as 95% inhibition at 0.5 mM concentration. A plateau effect was observed as the concentration of TD-7 was increased. The water soluble HCl salt of TD-7 interestingly barely showed any antisickling effect at 0.5 mM, but remarkably inhibited 100% sickling at 1.0 mM showing a plateau with increasing drug concentration. INN-312, the second-generation positive control, also decreased the percent of sickled cells in a dose-dependent manner but at 0.5 mM it only inhibited sickling to 15% compared to the 95% by TD-7. TD-7-1, the ester nitrate of TD-7 although preventing RBC sickling, hemolyzed the RBC at higher drug concentrations. Also, it seems to swell/hydrate the RBC due to possible intracellular uptake of water which could be beneficial to counteract the rigidity of sickle cells. TD-8 and TD-9 were not as potent as the TD-7 analog, only inhibiting 38 and 57% RBC sickling, respectively at 2 mM. In comparison, vanillin which is the parent scaffold for the INN and TD compounds only inhibited 12% RBC sickling at 5 mM.

REFERENCES

1 Wishner, B. C.; Ward, K. B.; Lattman, E. E.; Love, W. E. Crystal structure of sickle-cell deoxyhemoglobin at 5 Å resolution. *J. Mol. Biol.* 1975, 98, 179-194.

2 Vekilov, P. G. Sickle-cell haemoglobin polymerization: Is it the primary pathogenic event of sickle-cell anaemia? *Br. J. Haematol.* 2007, 139, 173-184.

3 Abdulmalik, O.; Safo, M. K.; Chen, Q.; Yang, J.; Brugnara, C.; Ohene-Frempong, K.; Abraham, D. J.; Asakura, T. 5-Hydroxymethyl-2-furfural modifies intracellular sickle haemoglobin and inhibits sickling of red blood cells. *Br. J. Haematol.* 2005, 128, 552-561.

4 Nnamani, I. N.; Joshi, G. S.; Danso-Danquah, R.; Abdulmalik, 0.; Asakura, T.; Abraham, D. J.; Safo, M. K. Pyridyl derivatives of benzaldehyde as potential antisickling agents. *Chem. Biodivers.* 2008, 5, 1762-1769.

5 Abdulmalik, O.; Safo, M. K.; Chen, Q.; Yang, J.; Brugnara, C.; Ohene-Frempong, K.; Abraham, D. J.; Asakura, T. 5-Hydroxymethyl-2-furfural modifies intracellular sickle haemoglobin and inhibits sickling of red blood cells. *Br. J. Haematol.* 2005, 128, 552-561.

6 Abdulmalik, O.; Ghatge, M. S.; Musayev, F. N.; Parikh, A.; Chen, Q.; Yang, J.; Nnamani, I.; Danso-Danquah, R.; Eseonu, D. N.; Asakura, T.; Abraham, D. J.; Venitz, J.; Safo, M. K. Crystallographic analysis of human hemoglobin elucidates the structural basis of the potent and dual antisickling activity of pyridyl derivatives of vanillin. *Acta Crystallogr. D: Biol. Crystallogr.* 2011, 67, 920-928.

7 Parikh, A.; Ghatge, M.; Safo, M; Venitz, J. Comparative pharmacodynamic (PD) profiling of the in-vitro time- and concentration-dependent effects of known, synthetic allosteric effectors of hemoglobin (AEH). Presented at the 2011 American Association of Pharmaceutical Scientists (AAPS) Annual Meeting and Exposition, Washington, D.C., October 2011.

8 Rees, D. C.; Williams, T. N.; Gladwin, M. T. Sickle-cell disease. *The Lancet* 2010, 376, 2018-2031.

9 Sun, K.; Xia, Y. New insights into sickle cell disease: A disease of hypoxia. *Curr. Opin. Hematol.* 2013, 20, 215-221.

10 Ricart-Jane, D.; Llobera, M.; Lopez-Tejero, M. D. Anticoagulants and other preanalytical factors interfere in plasma nitrate/nitrite quantification by the griess method. *Nitric Oxide* 2002, 6, 178-185.

11 Mack, A. K.; Kato, G. J. Sickle cell disease and nitric oxide: A paradigm shift? *Int. J. Biochem. Cell Biol.* 2006, 38, 1237-1243.

12 Girgis, R. E.; Qureshi, M. A.; Abrams, J.; Swerdlow, P. Decreased exhaled nitric oxide in sickle cell disease: Relationship with chronic lung involvement. *Am. J. Hematol.* 2003, 72, 177-184.

13 Hunter, C. J.; Dejam, A.; Blood, A. B.; Shields, H.; Kim-Shapiro, D. B.; Machado, R. F.; Tarekegn, S.; Mulla, N.; Hopper, A. O.; Schechter, A. N.; Power, G. G.; Gladwin, M. T. Inhaled nebulized nitrite is a hypoxia-sensitive NO-dependent selective pulmonary vasodilator. *Nat. Med.* 2004, 10, 1122-1127.

14 Weiner D. L.; Hibberd, P. L.; Betit, P.; Cooper, A. B.; Botelho, C. A.; Brugngra, C. Preliminary assessment of inhaled nitric oxide for acute vaso-occlusive crisis in pediatric patients with sickle cell disease. *JAMA* 2003, 289, 1136-1142.

15 Miller, M. R.; Megson, I. L. Recent developments in nitric oxide donor drugs. *Br. J. Pharmacol.* 2007, 151, 305-21.

16 de Franceschi, L.; Baron, A.; Scarpa, A.; Adrie, C.; Janin, A.; Barbi, S.; Kister, J.; Rouyer-Fessard, P.; Corrocher, R.; Leboulch, P.; Beuzard, Y. Inhaled nitric oxide protects transgenic sad mice from sickle cell disease-specific lung injury induced by hypoxia/reoxygenation. *Blood* 2003, 102, 1087-1096.

17 Kahn, M. J.; Maley, J. H.; Lasker, G. F.; Kadowitz, P. J. Updated role of nitric oxide in disorders of erythrocyte function. *Cardiovasc. Hematol. Disord. Drug Targets* 2013, 13, 83-87.

18 Perutz, M. F. Structure and mechanism of haemoglobin. *Br. Med. Bull.* 1976, 32, 195-208.

19 Stea, B.; Shaw, E.; Pinter, T.; Hackman, J.; Craig, M.; May, J.; Steffen, R. P.; Suh, J. H. Efaproxiral red blood cell concentration predicts efficacy in patients with brain metastases. *Br. J. Cancer* 2006, 94, 1777-1784.

20 Bunn, H. F. & Forget, G. B. Hemoglobin: Molecular, Genetic and Clinical Aspects. 1986, p 462, W. B. Saunders company.

What is claimed is:

1. A compound having the formula:

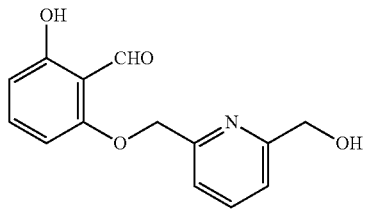 [SMILES: O=Cc1c(O)cccc1OCc1cccc(CO)n1]

and pharmaceutically acceptable salts thereof.

2. A compound having the formula:

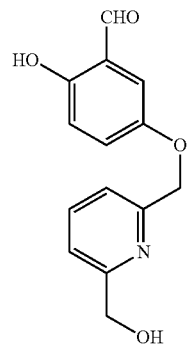 [SMILES: O=Cc1cc(OCc2cccc(CO)n2)ccc1O]

and pharmaceutically acceptable salts thereof.

* * * * *